United States Patent
Reed et al.

(10) Patent No.: US 6,949,561 B1
(45) Date of Patent: Sep. 27, 2005

(54) STEROID 3-O-SULPHAMATE DERIVATIVES AS INHIBITORS OF OESTRONE SULPHATASE

(75) Inventors: Michael John Reed, London (GB); Barry Victor Lloyd Potter, Bath (GB)

(73) Assignee: Sterix Limited, Oxford (GB)

( * ) Notice: Subject to any disclaimer, the term of this patent is extended or adjusted under 35 U.S.C. 154(b) by 0 days.

(21) Appl. No.: 09/572,246

(22) Filed: May 17, 2000

Related U.S. Application Data

(63) Continuation-in-part of application No. PCT/GB98/03616, filed on Dec. 3, 1998.

(30) Foreign Application Priority Data

Dec. 4, 1997 (GB) .............................. 9725750

(51) Int. Cl.$^7$ ................... A61K 31/435; C07D 221/18
(52) U.S. Cl. ................... 514/284; 514/453; 546/61; 549/277
(58) Field of Search ................... 546/61; 549/277; 514/284, 453

(56) References Cited

U.S. PATENT DOCUMENTS

| | | | |
|---|---|---|---|
| 4,155,918 A | 5/1979 | Furst et al. | |
| 4,178,381 A | 12/1979 | Haffer | |
| 4,200,636 A | * 4/1980 | Tuba et al. | ................ 424/250 |
| 4,874,891 A | 10/1989 | Covey | |
| 5,260,299 A | 11/1993 | Failli et al. | |
| 5,391,776 A | 2/1995 | Ueno | |
| 5,604,215 A | 2/1997 | Reed et al. | |
| 5,616,574 A | 4/1997 | Reed et al. | |
| 5,830,886 A | 11/1998 | Reed et al. | |
| 5,861,390 A | 1/1999 | Reed et al. | |
| 6,011,024 A | 1/2000 | Reed et al. | |
| 6,017,904 A | 1/2000 | Reed et al. | |
| 6,083,978 A | 7/2000 | Reed et al. | |
| 6,087,347 A | 7/2000 | Koizumi et al. | |
| 6,159,960 A | 12/2000 | Reed et al. | |
| 6,187,766 B1 | 2/2001 | Reed et al. | |
| 6,239,169 B1 | 5/2001 | Reed et al. | |
| 6,339,079 B1 | 1/2002 | Kasch et al. | |

FOREIGN PATENT DOCUMENTS

| | | |
|---|---|---|
| AU | 199742191 | 9/1997 |
| EP | 0 111 746 | 6/1984 |
| EP | 0 403 185 | 12/1990 |
| EP | 0 934 949 | 8/1999 |
| WO | WO 85/05361 | 12/1985 |
| WO | WO 93/20078 | 10/1993 |
| WO | WO 97/05126 | 2/1997 |
| WO | WO 97/30041 | 8/1997 |
| WO | WO 97/32872 | 9/1997 |
| WO | WO 98/11124 | 3/1998 |
| WO | WO 98/24802 | 6/1998 |
| WO | WO 00/18397 | 4/2000 |

OTHER PUBLICATIONS

Meyers et al., J Med. Chem 42:2456–68 (1999).
Chemical Abstracts, vol. 128, No. 21, Abstract No. 257603 (1998).
Chemical Abstracts, 126:528 (1996).

* cited by examiner

*Primary Examiner*—Patricia L. Morris
(74) *Attorney, Agent, or Firm*—Frommer Lawrence & Haug LLP; Thomas J. Kowalski

(57) ABSTRACT

A sulphamate compound suitable for use as an inhibitor of oestrone sulphatese (E.C.3.1.6.2) is described. The compound is a polycyclic compound comprising at least two ring components, wherein the polycyclic compound comprises at least one sulphamate group attached to at least one of the ring components, and wherein at least one of the ring components of the polycyclic structure is a heterocyclic ring.

19 Claims, No Drawings

STEROID 3-O-SULPHAMATE DERIVATIVES AS INHIBITORS OF OESTRONE SULPHATASE

This application is a continuation-in-part of PCT/GB98/03616, filed Dec. 3, 1998 and designating the U.S., and published as WO 99/27935, on Jun. 10, 1999 and claiming priority from British application 9725750.5, filed Dec. 4, 1997. Reference is also made to U.S. Pat. Nos. 6,017,904, 6,011,024, 5,861,390, 5,830,886, 5,616,574, and 5,604,215 and allowed application Ser. Nos. 09/125,255, filed Aug. 14, 1998, and 09/142,194, filed Sep. 2, 1998. Each of the foregoing applications, patents and publications and all documents cited or referenced therein ("application cited documents") and all documents cited or referenced in this specification ("herein cited documents") and all documents referenced or cited in herein cited documents and in application cited documents, including during the prosecution of any of the application cited documents, are hereby incorporated herein by reference.

The present invention relates to a compound.

In particular the present invention relates to a compound and to a pharmaceutical composition comprising the compound. The present invention also relates to the use of that compound in the field of medicine.

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In sinu synthesis of oestrogen is thought to make an important contribution to the high levels of oestrogens in trumours and therefore specific inhibitors of oestrogen biosynthesis are of potential value for the treatment of endocrine-dependent tumours.

Over the past two decades, there has been considerable interest in the development of inhibitors of the aromatase pathway which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours. This theory is supported by a modest reduction of plasma oestrogen concentration in postmenopausal women with breast cancer treated by aromatase inhibitors, such as aminoglutethicide and 4-hydroxyandrostenedione and also by the fact that plasma E1S concentration in these aromatase inhibitor-treated patients remains relatively high. The long half-life of E1S in blood (10–12 h) compared with the unconjugated oestrogens (20 min) and high levels of steroid sulphatase activity in liver and, normal and malignant breast tissues, also lend support to this theory. PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters. Examples of such inhibitors are sulphamate ester derivatives of steroids.

As is well known in the art, steroids have the general formula of:

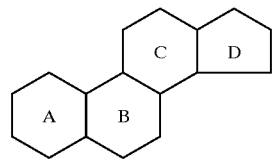

In the above formula, the ring components have been labelled in the conventional manner.

A preferred compound of PCT/GB92/01587 is oestrone-3-sulphamate (otherwise known as "EMATE"), which has the following structure:

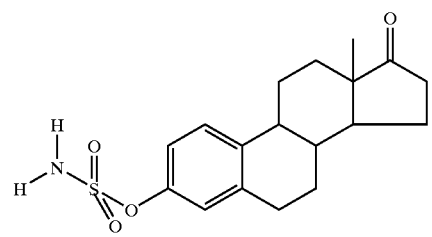

It is known that EMATE is a potent E1-STS inhibitor as it displays more than 99% inhibition of E1-STS activity in intact MCF-7 cells at 0.1 $\mu$M. EMATE also inhibits the E1-STS enzyme in a time- and concentration-dependent manner, indicating that it acts as an active site-directed inactivator.

Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms—as in oestrone-3-N-sulphamate and oestrone-3-S-sulphamate—these analogues are weaker non-time-dependent inactivators.

Although optimal potency for inhibition of E1-STS may have been attained in EMATE, it is possible that oestrone may be released during sulphatase inhibition, and that EMATE and its oestradiol congener may possess oestrogenic activity.

The present invention seeks to provide novel compounds suitable for the inhibition of E1-STS but preferably wherein those compounds have no, or a minimal, oestrogenic effect.

Certain aspects of the present invention are presented in the accompanying claims.

A key advantage of the present invention is that the sulphamate compounds of the present invention can act as E1-STS inhibitors.

Another advantage of the compounds of the present invention is that they may be potent in vivo and that they may have less oestrogenic activity than the known compounds and can therefore be deemed to be "non-oestrogenic compounds". The term "non-oestrogenic compound" as used herein means a compound exhibiting no or substantially no oestrogenic activity.

The present invention therefore provides sulphamate compounds which may have a reduced oestrogenic activity.

Another advantage is that the compounds may not be capable of being metabolised to compounds which display or induce hormonal activity.

The compounds of the present invention are also advantageous in that they may be orally active.

The compounds of the present invention are further advantageous in that they may have an irreversible effect.

In a preferred embodiment, the sulphamate compounds of the present invention are useful for the treatment of breast cancer, or endocrine-dependent cancers, or endocrine- or oestrogen-dependent conditions and/or illnesses and/or cancers; see also documents cited herein (compounds therein also so useful). In addition, the sulphamate compounds of the present invention are useful for the treatment of non-malignant conditions, such as the prevention of auto-immune diseases, particularly when pharmaceuticals may need to be administered from an early age.

The sulphamate compounds of the present invention are also believed to have therapeutic uses other than for the treatment of endocrine-dependent cancers, such as the treatment of autoimmune diseases.

These and further aspects of the present invention are now described.

Some or all of the ring components may be fused together or joined via one or more suitable spacer groups. The present invention also encompasses combinations thereof.

The term "sulphamate" as used herein includes an ester of sulphamic acid, or an ester of an N-substituted derivative of sulphamic acid, or a salt thereof.

Preferably, the sulphamate group has the formula:

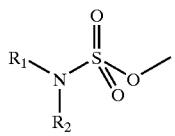

wherein each of $R_1$ and $R_2$ is independently selected from H or a hydrocarbyl group.

The term "hydrocarbyl group" as used herein means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred embodiment of the present invention, the hydrocarbyl group is a hydrocarbon group.

Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably $R_1$ and $R_2$ are independently selected from H or alkyl, cycloalkyl, alkenyl and aryl, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R_1$ and/or $R_2$ is alkyl, the preferred values are those where $R_1$ and $R_2$ are each independently selected from lower alkyl groups containing from 1 to 5 carbon atoms, that is to say methyl, ethyl, propyl etc. Preferably $R_1$ and $R_2$ are both methyl. When $R_1$ and/or $R_2$ is aryl, typical values are phenyl and tolyl (—PhCH$_3$; o-, m- or p-). Where $R_1$ and $R_2$ represent cycloalkyl, typical values are cyclopropyl, cyclopentyl, cyclohexyl etc. When joined together $R_1$ and $R_2$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino.

Within the values alkyl, cycloalkyl, alkenyl and aryl we include substituted groups contining as substituents therein one or more groups which do not interfere with the sulphatase inhibitory activity of the compound in question. Exemplary non-interfering substituents include hydroxy, amino, halo, alkoxy, alkyl and aryl. A non-limiting example of a hvdrocarbyl group is an acyl group.

In some preferred embodiments, at least one of $R_1$ and $R_2$ is H.

The polycyclic compound can comprise at least two ring components, or least three ring comnponents, or least four ring components.

Preferably, the polycyclic compound comprises four ring components.

Preferably the polycyclic compound will contain, inclusive of all substituents, no more than 50 about carbon atoms, more usually no more than about 30 to 40 carbon atoms.

Preferred polycyclic compounds are those that are based on steroidal ring structures, that is to say a cyclopentanophenanthrene skeleton.

Thus, a preferred polycyclic compound of the present invention has a structure similar to a steroidal structure but wherein the D ring is a heterocyclic ring.

In this regard, the structure of a preferred polycyclic compound can be presented as:

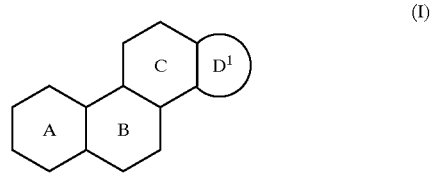

(I)

wherein ring $D^1$ represents a heterocyclic group, which may be substituted; and wherein rings A, B and C are rings normally associated with a steroidal nucleus—which rings may be substituted or unsubstituted, saturated or unsaturated.

A preferred example of $D^1$ is a six membered heterocyclic ring.

Preferably the heterocylic ring comprises a combination of C atoms and at least one N atom and/or at least one O atom. Other heterocyclic atoms may be present in the ring.

The heterocyclic ring coinponent of $D^1$ may be substituted with suitable groups—such as alkyl, hydroxy, halo, a hydrocarbyl group etc. However, in a preferred embodiment, the heterocyclic ring is unsubstituted.

Preferred heterocyclic rings are or comprise a lactone or a lactam, or substituted derivatives thereof and/or unsaturated derivatives thereof. The substituted derivatives include substitutions on the N of the heterocyclic ring (if the ring comprises a N atom) and/or on one or more of the C of the heterocyclic ring. Exarnples of substituents include one or more of halo, hydroxy, hydrocarbyl, carboxy, alkoxy.

Preferred heterocyclic rings are or comprise a lactone or a lactam.

Examples of suitable, preferred steroidal nuclei rings A–C of the compounds of the present invention include rings A–C of oestrone and dehydroepiandrosterone.

Preferred steroidal nuclei rings A–C of the compounds of the present invention include rings A–C of:
oestrones and substituted oestrones, viz:
oestrone
2-OH-oestrone
2-methoxy-oestrone
4-OH-oestrone
6α-OH-oestrone
7α-OH-oestrone
16α-OH-oestrone
16b-OH-oestrone
oestradiols and substituted oestradiols, viz:
2-OH-17β-oestradiol
2-methoxy-17β-oestradiol
4-OH-17β-oestradiol
6α-OH-17β-oestradiol
7α-OH- 17β-oestradiol
16α-OH-17β-oestradiol
16β-OH-17α-oestradiol
16β-OH-17β-oestradiol
17α-oestradiol
17β-oestradiol
17α-ethinyl-17β-oestradiol
oestriols and substituted oestriols, viz:
oestriol
2-OH-oestriol
2-methoxy-oestriol
4-OH-oestriol
6α-OH-oestriol
7α-OH-oestriol
dehydroepiandrosterones and substituted
  dehydroepiandrosterones, viz:
dehydroepiandrosterones
6α-OH-dehydroepiandrosterone
7α-OH-dehydroepiandrosterone
16α-OH-dehydroepiandrosterone
16β-OH-dehydroepianidrosterone In general terms the ring system $ABCD^1$ may contain a variety of non-interfering substituents. In particular, the ring system $ABCD^1$ may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

In an alternative emibodiment, the polyclic compound may not contain or be based on a steroid nucleus. In this regard, the polyclic compound may contain or be based on a non-steroidal ring system—such as diethylstilboestrol, stilboestrol and other ring systems.

In formula (I), the at least one sulphamate group is attached to any one or more of the ring components.

Preferably, the polycyclic compound has a steroidal structure and wherein the sulphamate group is attached to the A ring.

Preferably, the sulphamate group is attached to the 3 position of the A ring. i5 A prefe ompound has the formula: wherein R denotes a lphamate group as described above. Here the indicated Me group is vertical. Preferably, R is the above- entioed preferred formula for the sulphamate group. In is this regard, it is preferred that east one of R, and R, is H. An alternative preferred compouneas the formula: H Me I 20 wherein R denotes a sulpharnate group as desribed above. Here the indicated Me group is vertical.

SUBS 10 TE SHEET (RULE 26) 09572246 - SPEC Page 10 of 42 (05-17-2000)

Preferably, R is the above-mentioed preferred formula for the sulphamate group. In this regard, it is preferred that at least one of $R_1$ and $R_2$ is H.

Preferably, if the sulphamate group of the compound were to be replaced with a sulphate group to form a sulphate compound then that sulphate compound would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound, then that sulphate compund would be hydrolysable by an enzyme having steroid sulphatase activity (E.C. 3.1.6.2), and would yield a $K_m$ value of less than 50 mM when incubated with steroid sulphatase at pH 7.4 and 37° C.

In another preferred embodiment, if the sulphamate group of the compound were to be replaced with a sulphate group to form a sulphate compound, then that sulphate compund would be hydrolysable by an enzyme having steroid sulphatase activity (E.C. 3.1.6.2), and optionally would yield a $K_m$ value of less than 50 $\mu$M when incubated with sulphatase at pH 7.4 and 37° C.

In a highly preferred embodiment, the compound of the present invention is not hydrolysable by an enzyme having steroid sulphatase (E.C. 3.1.6.2) activity.

The sulphamate compounds of the present invention may be prepared by reacting an appropriate alcohol with the appropriate sulfamoyl chloride, $R_1R_2NSO_3Cl$.

Preferred conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

For pharmaceutical administration, the steroid sulphatase inhibitors of this invention can be formulated in any suitable manner utilising conventional pharmaceutical formulating techniques and pharmaceutical carriers, adjuvants, excipients, diluents etc. and usually for parenteral administration. Approximate effective dose rates are in the range 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

For particular applications, it is envisaged that the steroid sulphatase inhibitors of this invention may be used in combination therapies, either with another sulphatase inhibitor, or, for example, in combination with an aromatase inhibitor, such as for example, 4-hydroxyandrostenedione (4-OHA).

In the method of treatment, the subject is preferably a mammal, more preferably a human. For some applications, preferably the human is a woman.

In summation, the present invention provides novel compounds for use as steroid sulphatase inhibitors, and pharmaceutical compositions containing them. The compounds have a reduced oestrogenic activity—particularly when compared with EMATE. Thus, the compounds of the present invention are capable of acting as selective E1-STS inhibitors. Thus, the present invention provides novel compounds having steroid sulphatase inhibitory activity which, in some cases, have extremely high activity levels.

It will be appreciated that the present invention also includes the following:
(i) a compound of the present invention or a pharmaceutically acceptable salt of the compound, or a pharmaceutically acceptable solvate of the compound or the salt;
(ii) one or more processes for the preparation of a compound of the present invention or a pharmaceutically acceptable salt of the compound, or a pharmaceutically acceptable solvate of the compound or the salt;
(iii) novel intermediates for use in those processes;
(iv) a pharmaceutical composition comprising a compound of the present invention, or a pharmaceutically acceptable salt of the compound, or a pharmaceutically acceptable solvate of the compound or the salt, admixed with a pharmaceutically acceptable diluent, carrier or excipient;
(v) a compound of the present invention, or a pharmaceutically acceptable salt of the compound, or a pharmaceutically acceptable solvate of the compound or the salt or composition thereof, for use as a medicament;
(vi) the use of a compound of the present invention, or a pharmaceutically acceptable salt of the compound, or a pharmaceutically acceptable solvate of the compound or the salt or composition thereof, for the manufacture of a medicament for the inhibition of oestrone sulphatase;
(vii) the use of a compound of the present invention, or a pharmaceutically acceptable salt of the compound, or a pharmaceutically acceptable solvate of the compound or the salt or composition thereof, for the manufacture of a medicament for the inhibition of oestrone sulphatase;
(viii) a method for the inhibition of oestrone sulphatase which method comprises administering to a subject an effective amount of a compound of the present invention or a pharmaceutically acceptable salt of the compound, or a pharmaceutically acceptable solvate of the compound or the salt or composition thereof;
(ix) a method for inhibition of oestrone sulphatase which method comprises administering to a subject an effective amount of a compound of the present invention or a pharmaceutically acceptable salt of the compound, or a pharmaceutically acceptable solvate of the compound or the salt or composition thereof.

In the above-mentioned uses and methods, the subject is typically a mammal.

The pharmaceutically acceptable salts of the compounds of/for use in the present invention include suitable acid addition or base salts thereof. For a review on suitable pharmaceutical salts see Berge et al, J Pharm Sci, 66, 1–19 (1977).

By way of example, suitable acid addition salts are formed from acids which form non-toxic salts. Suitable examples of such salts are the hydrochloride, hydrobromide, hydroiodide, sulphate, bisulphate, phosphate, hydrogen phosphate, acetate, maleate, futmarate, lactate, tartrate, citrate, gluconate, benzoate, methanesulphonate, benzenesulphonate and p-toluenesulphonate salts.

Also by way of example, suitable base salts are formed from bases which form non-toxic salts. Suitable examples thereof are the aluminium, calcium, lithium, magnesium, potassium, sodium, zinc, N-benzyl-N-(2-phenylethyl) amine, 1-adamantylamine and diethanolamine salts.

As mentioned above, the present invention also covers pharmaceutical compositions comprising the compounds of the present invention. In this regard, and in particular for human therapy, even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice.

By way of example, in the pharmaceutical compositions of the present invention, the compounds of the present invention may be admixed with any suitable binder(s), lubricant(s), suspending agent(s), coating agent(s), solubilising agent(s).

Tablets or capsules of the compounds may be administered singly or two or more at a time, as appropriate. It iis also possible to administer the compounds in sustained release formulations.

Typically, a physician will determine the dosage which will be most suitable for an individual patient and it will vary with the age, weight and response of the particular patient.

Alternatively, the compounds of/for use in the present invention can be administered by inhalation or in the form of a suppository or pessary, or they may be applied topically in the form of a lotion, solution, cream, ointmnent or dusting powder. An alternative means of transdermnal administration is by use of a skin patch. For example, they can be incorporated into a cream consisting of an aqueous emulsion of polyethylene glycols or liquid paraffin. They can also be incorporated, such as at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either salone or in admixture with excipients, or in the form of elixirs, solutions or suspensions containing flavouring or colouring agents.

The compositions (as well as the compounds alone) can also be injected parenterally, for example intracavernosaly, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the compounds of the present invention and their pharmaceutically acceptable salts and solvates may typically be from 10 to 500 mg (in single or divided doses). Thus, and by way of example, tablets or capsules may contain from 5 to 100 mg of active compound for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

Thus the invention provides a pharmaceutical composition comprising a compound of the present invention, or a pharmaceutically acceptable salt thereof, or a pharmaceutically acceptable solvate of either entity, together with a pharmaceutically acceptable diluent, excipient or carrier.

The invention further provides a compound of the present invention, or a pharmaceutically acceptable salt thereof, or a pharmaceutically acceptable solvate of either entity, or a pharmaceutical composition containing any of the foregoing, for use as a human medicament.

The present invention also provides a veterinary formulation comprising a compound of the present invention, or a veterinarily acceptable salt thereof, or a veterinarily acceptable solvate of either entity, together with a veterinarily acceptable diluent, excipient or carrier.

For veterinary use, a compound of the present invention or a veterinarily acceptable salt thereof, or a veterinarily acceptable solvate of either entity, is typically administered as a suitably acceptable formulation in accordance with normal veterinary practice and the veterinary surgeon will determine the dosing regimen and route of administration which will be most appropriate for a particular animal. However, as with human treatment, it may be possible to administer the compound alone for veterinary treatments.

In addition, the present invention provides a compound of the present invention, or a veterinarily acceptable salt thereof, or a veterinarily acceptable solvate of either entity, or a veterinary formulation containing any of the foregoing, for use as an animal medicament.

Reference is also made to WO 99/27936, and concurrently-filed U.S. application Ser. No. 09/572,237.

In the examples reference is made to steroid sulphatase inhibition. This is determined according to the teachings of PCT/GB92/01587 wherein the ability of compounds to inhibit oestrone sulphatase activity is assessed using either intact MCF-7 breast cancer cells or placental microsomes. For ease of reference, those teachings are repeated here as Example 1.

EXAMPLE 1

Inhibition of Steroid Sulphatase Activity in MCF-7 Cells by Oestrone-3-sulphamate.

Steroid sulphatase (Steroid sulphatase is defined as: Steryl Sulphatase EC 3.1.6.2.) activity was measured in vitro using intact MCF-7 human breast cancer cells. This hormone dependent cell line is widely used to study the control of human breast cancer cell growth. It possesses significant steroid sulphatase activity (MacIndoe et al. *Endocrinology*, 123, 1281–1287 (1988); Purohit & Reed, *Int. J. Cancer*, 50, 901–905 (1992)) and is available in the U.S.A. from the American Type Culture Collection (ATCC) and in the U.K. (e.g. from The Imperial Cancer Research Fund). Cells were maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 $cm^2$ tissue culture flasks were seeded with approximately $1 \times 10^5$ cells/flask using the above medium. Cells were grown to 80% confluency and medium was changed every third day.

Intact monolayers of MCF-7 cells in triplicate 25 $cm^2$ tissue culture flasks were washed with Earle's Balanced Salt Solution (EBSS from ICN Flow, High Wycombe, U.K.) and incubated for 3–4 hours at 37° C. with 5 pmol ($7 \times 10^5$ dpm) [6,7-$^3$H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0;1 fM; 0.01 pM; 0.1 pM; 1 pM; 0.01 nM; 0.1 nM; 1 nM; 0.01 mM; 0.1 mM; 1 mM). After incubation each flask was cooled and the medium (1 ml) was pipetted into separate tubes containing [$^{14}$C] oestrone ($7 \times 10^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C] oestrone and <0.1% [$^3$]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate. Each batch of experiments included incubations of microsomes prepared from a sulphatase-positive human placenta (positive control) and flasks without cells (to assess apparent non-enzymatic hydrolysis of the substrate). The number of cell nuclei per flask was determined using a Coulter Counter after treating the cell monolayers with Zaponin. One flask in each batch was used to assess cell membrane status and viability using the Trypan Blue exclusion method (Phillips, H. J. (1973) In: *Tissue culture and applicanons*, [eds: Kruse, D. F. & Patterson, M. K.]; pp. 406–408; Academic Press, New York).

Results for steroid sulphatase activity are expressed as the mean ±1 S.D. of the total product (oestrone+oestradiol) formed during the incubation period (20 hours) calculated for $10^6$ cells and, for values showing statistical significance, as a percentage reduction (inhibition) over incubations containing no oestrone-3-sulphamate. Unpaired Student's t-test was used to test the statistical-significance of results.

Inhibition of Steroid Sulphatase Activity in Placental Microsomes by Oestrone-3-sulphamate Sulphatase-positive human placenta from normal term pregnancies (Obstetric Ward, St. Mary's Hospital, London) were thoroughly minced with scissors and washed once with cold phosphate buffer (pH 7.4, 50 mM) then re-suspended in cold phosphate buffer (5 ml/g tissue). Homogenisation was accomplished with an Ultra-Turrax homogeniser, using three 10 second bursts separated by 2 minute cooling periods in ice. Nuclei and cell debris were removed by centrifuging (4° C.) at 2000 g for 30 minutes and portions (2 ml) of the supernatant were stored at −20° C. The protein concentration of the supernatants was determined by the method of Bradford (*Anal. Biochem.*, 72, 248–254 (1976)).

Incubations (1 ml) were carried out using a protein concentration of 100 mg/ml, substrate concentration of 20 mM [6,7-$^3$H]oestrone-3-sulphate (specific activity 60 Ci/mmol from New England Nuclear. Boston, Mass., U.S.A.) and an incubation time of 20 minutes at 37° C. Eight concentrations of the compounds to be tested may be employed: 0 (i.e. control); 0.05 mM; 0.1 mM; 0.2 mM; 0.4 mM; 0.6 mM; 0.8 mM; 1.0 mM. After incubation each sample was cooled and the medium (1 ml) was pipetted into separate tubes containing [$^{14}$C]oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C]oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate.

EXAMPLE 2

Oestralactam

Initially, we prepared oestrone oxime according to the method described[3], but we used hydroxylamine hydrochloride instead of hydroxylamine acetate and obtained oestrone oxime in excellent yield, better than previously reported.

Of two possible geometrical isomers for 17-oximes, Wataru et al.[4] assumed they had the anti-form, because it is believed that this form of oximes[5] is more stable than the syn-form and that the transition state leading to the anti-oxime may have an energy lower to that in the case of the syn-isomer. Thus, the structure of the oestrone oxime isomer obtained was just assumed, and not confirmed by any special method such as NOE or X-ray crystallography. To prove and confirm which isomer was obtained from the reaction, we ran NOE experiment which did not work; perhaps because the hydroxyl group of the oxime is exchangeable. We proved the structure of oestrone oxime by X-ray -crystallography and it was found indeed that only one geometrical isomer (anti-oxime isomer) was obtained.

Our study is the first to provide modern spectroscopic data and an X-ray crystal structure for oestrone oxime.

CHN analysis for oestrone oxime was alright, but by considering a small methanol content (from the crystallization solvent), which involved in hydrogen bonding to the molecule as X-ray shows, then the CHN values are very close.

The lactam form the anti-oxime of oestrone was prepared according to the method described[3] to give oestralactam 2 as the only possible structure. Bernard et al.[3] proved the same structure by opening the lactam ring to form a primary carboxylic acid, not a tertiary carboxylic acid, as if the other isomer were formed. The primary carboxylic acid was readily esterified with methanol and an acid catalyst. But this was not enough evidence to prove the structure of oestrone lactam. Our modem methods to prove the structure of the oestrone oxime are more solid and show only the oestralactam.

Our study is also the first to provide modern spectroscopic data for oestralactam.

Due to the extremely insolubility of the oestrolactam and its high melting point, it could not be recrystallized from the usual organic solvents, and purity determination by TLC and accurate mass spectroscopy was correct, but CHN values is quite out of the range, although if we consider the presence of two molecules of methanol from the solvent by hydrogen bonding to the phenol of ring A and to the proton of the lactam of ring D, which is certainly feasible, as happens in oestrone oxime by X-ray crystal structure, the CHN is alright. Heating is required to dissolve the oestralactam in DMF (the reaction solvent of sulphamylation) to prepare oestralactam sulphamate [4].

Oestrone Oxime (1)

To a solution of oestrone (10 g, 36.982 mmol) in ethanol (300 ml), hydroxylamine hydrochloride (7.71 g, 111 mmol, 3 eq.), sodium hydroxide (3.0 g, 75 mmol, 2 eq.) and water (10 ml) were added. The mixture was refluxed for two hours. The cold mixture was poured into 1N HCl. The precipitate was filtered, washed with cold water and dried to give a white solid (10.132 g, 96%). For analysis, a sample was recrystallized from aqueous methanol to give 1 as colorless crystals. Mp.=249–251° C. (lit. Mp.=248–250° C.), IR (KBr) 1690 (—C=N—) cm$^{-1}$. $\delta_H$ (DMSO-d$_6$, 400 MHz) 0.85 (3H, s, C-18-CH$_3$), 1.26–3.18 (15H, m), 6.44 (1H, d, $J_{C-4-H\ and\ C-2-H}$=2.13 Hz, C-4-H), 6.5 (1H, dd, $J_{C-2-H\ and\ C-1-H}$=8.24 Hz and $J_{C-2-H\ and\ C-4-H}$=2.44 Hz, C-2-H) 7.04 (1H, d, $J_{C-1-H\ and\ C-2-H}$=8.55 Hz, C-1-H), 9.03 (1H, br s, C-3-OH) and 10.1 (1H, br s, C=N—OH). C$^{13}$ 167.99 (—C=N—), 155.025 (C-3), 137.103 (C-5 or C-10), 130.19 (C10 or C-5), 126.0 (C-1), 114.99 (C-4), 112.79 (C-2), 52.52 (C-8 or C-14), 48.66 (CH$_3$ from methanol), 43.62 (C-8 or C-9 or C-9 C-9 or C-14), 43.61 (C-13), 37.91 (C-8 or C-9 or C-14), 34.33, 29.13, 26.90, 25.99, 24.94 and 22.57 (C-6, C-7, C-11, C-12, C-15 and C-16) and 17.35 (C-18). MS: m/z (+ve ion FAB in m-NBA, rel. intensity) 439.3 [15, (M+H+NBA)$^+$], 286.3 [100, M+H)$^+$], 268.3 [20, (M−H$_2$O)], 243.3 (10), 178.2 (10) 159.1 (10), 133.1 (15), 102.0 (10) and 74.9 (10). MS: m/z (−ve ion FAB in m-NBA, rel. intensity) 437.3 [65, (M−H+NBA)$^+$], 284.2 [100, (M−H)], 258.1 (25), 229.1 (20), 215.1 (25), 195.1 (45), 178.1 (30), 139.1 (35), 108.0 (30) and 65.0 (10). Acc. MS: m/z (FAB)$^+$=286.18046 C$_{18}$H$_{24}$NO$_2$ requires 286.18072. Found C, 73.5; H, 8.27; N, 4.48; C$_{18}$H$_{23}$NO$_2$ requires C, 75.76; H, 8.12; N, 4.91.

3-Hydroxy-13α-amino-13,17-seco-1,3,5(10)-estratrien-17-oic 13,17-lactam (17a-Aza-D-homoestrone) (Oestronelactam) (3)

A Solution of oestrone oxime (1.0 g, 3.504 mmol), in anhydrous dioxane (35 ml) at 40° C. was stirred as thionyl chloride (1 ml) was added dropwise. A white precipitate which became yellow and then light brown, formed as the temperature rose to 49° C. After stirring ten minutes longer, the reaction mixture was quenched and made slightly alkaine by slow addition of aqueous sodium hydrogencarbonate solution. The resulting precipitate was filtered, washed with water and dried to give a yellow solid. Then it was triturated with methanol for decolourization and discarded imnpurities used. The precipitate was filtered and dried to give the lactam 3 as an almost white powder (733 mg, 73%). mp.=>350° C. (lit. 373–377° C. (dec.)). IR (KBr) 1640 (—CO—) cm$^{-1}$. $\delta_H$ (DMSO-d$_6$, 400 MHz) 1.07 (3H, s, C-18-CH$_3$), 1.12–2.71 (15H, m ), 6.44 (1H, d, $J_{C-4-H\ and\ C-2-H}$=2.45 Hz, C-4-H), 6.51 (1H, dd, $J_{C-1-H\ and\ C-1-H}$=8.31 Hz and $J_{C-2-H\ and\ C-4-H}$=2.45 Hz. C-2-H), 7.05 (1H, d $J_{C-1-H\ and\ C-2-H}$=8.31 Hz, C-1-H), 7.56 (1H, br s, NH) and 9.02 (1H, br s, C-3-OH). MS: m/z (+ve ion FAB in m-NBA, rel. intensity) 286.2 [100, (M+H)+], 270.2 (10), 255.2 (15), 243.2 (10), 225.2 (5), 213.1 (5), 195.1 (5), 183.1 (10), 173.2 (15), 157.1 (10), 145.1 (10), 131.1 (10), 111.0 (10), 97.0 (15), 79.9 (10) and 63.9 (10). Acc. MS: m/z (FAB)+=286.1812 $C_{18}H_{24}NO_2$ requires 286.1807. Found C, 69.9; H, 7.44; N, 4.41; $C_{18}H_{23}NO_2$ requires C, 75.76; H, 8.12; N, 4.91.

3-O-Sulphamyl-13α-amino-13,17-seco-1,3,5(10)-estratrien-17-oic 13,17-lactam (4)

Oestronelactam (272 mg, 0.9544 mmol) was added to anhydrous DMF (50 ml) and was heated till dissolved, the reaction mixture cooled to room temperature, then sodium hydride (57 mg, 1.5 eq.) was added in small portions and the reaction mixture was stirred under $N_2$ for half an hour. A concentrated sulphomyl chloride solution in toluene (5 eq.) was added. The reaction mixture was stirred overnight, poured into brine and extracted with ethyl acetate which was then washed with water, dried ($MgSO_4$) and after evaporated the solvent, gave a crude product (330 mg) which was fractionated on silica (100 g) with chloroform/acetone gradient, and upon evaporation the second fraction gave beige residue (286 mg) which was recrystallized from acetone/hexane (1:2) to give 4 as almost white crystals (223 mg, 64%) mp.=>265° C. (dec.). IR (KBr) 3500 ($NH_2$) 1710(CO), 1470 (—$SO_2$—) cm$^{-1}$. $\delta_H$ (DMSO-$d_6$, 400 MHz) 1.1 (3H, s, C-18-$CH_3$), 1.21–2.9 (15H, m), 6.98 (1H, d, $J_{C-4-H\ and\ C-2-H}$=2.14 Hz, C-4-H), 7.02 (1H, dd, $J_{C-2-H\ and\ C-1-H}$=8.54 Hz and J $_{C-2-H\ and\ C-4-H}$=2.14 Hz, C-2-H), 7.35 (1H, d, J $_{C-1-H\ and\ C-2-H}$=8.54 Hz, C-1-H), 7.6 (1H, br s, NH) and 7.94 (2H, s, exchanged with $D_2O$, C-3-$SO_2NH_2$). MS: m/z (+ve ion FAB in m-NBA, rel. intensity) 365.2 [100, (M+H)+], 349.2 (20), 330.1 (25), 319.1 (10), 306.1 (15), 287.1 [10, (M+H–$SO_2NH_2$)+]. MS: m/z (–ve ion FAB in m-NBA, rel. intensity) 517.2 [50, (M+NBA)+], 363.1 [100, (M–H)], 341.0 (30), 292.1 (20), 276.1 (40), 258.0 (35). Acc. MS: m/z (FAB)+=365.1550 $C_{18}H_{25}N_2O_4S$ requires 365.1535. Found C, 58.9; H, 6.61; N, 7.36; $C_{18}H_{23}N_2O_2S$ requires C, 59.32; H, 6.64; N, 7.69.

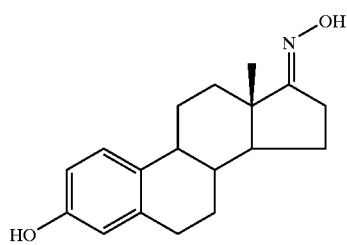

[1]

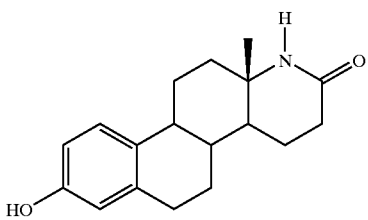

[3]

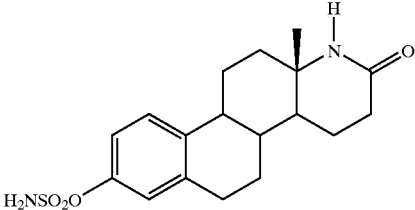

[4]

REFERENCES

1) Ivanenko T I, Kolomin L V, Golubovskaya L E and Pivnitskii KK. Synthesis and properties of 17-N-Substituted derivatives of 1,3,5 (10)-estratrienes. *Pharm. Chem. J.* 1982, 16, 751–56.
2) Peters R. H. Crowe D F, Mitchell A A, Chong W K M and Tanabe M. 17-Desoxy estrogen analogues. *J. Med. Chem.* 1989, 32, 1642–52.
3) Bernard M R and Hayes F N 17- and 17a-D-homosteroids. *Journal of American Chemical Society* 1955, 78, 639–643.
4) Nagata W, Sugasawa T, Narisada M, Okada T, Sasakura K, Murakami M and Hayase Y. Steroids and their O-alkyl derivatives. *Chem. Pharm. Bull.* 1966, 14, 174–186.
5) Kaufmann C S Beckmann rearrangement of 17-keto steroids oximes. *J. Am. Chem. Soc.* 1951, 73. 1779.

EXAMPLE 3

Steroid Lactones

The oxidation of a steroid ring ketone to a lactone was first reported by Garder and Godden using ammonium persulphate for oxidation of coprostan-3-one.

The conversion of a 17-keto steroid to a D ring lactone was first reported by Westerfeld[2] who oxidised estrone with alkaline hydrogen peroxide. Subsequently, Jacobsen[3] oxidised oestrone with peracid in acetic acid to a lactone which was chemically similar to westerfeld's lactone [1][a] but different in its physiological properties. Several related lactones have been also prepared by the microbiological oxidation of steroids[4,5].

Our modification of Westerfeld method[2] by using milder conditions and a longer reaction time gave estralactone in excellent yield (84%), the best and highest yield reported so far. Briefly, treatment of oestrone with alkaline 6% hydrogen-peroxide instead of 10% for 5–7 days not for 3 days at room temperature gave estralactone in high yield. The estralactone could not recrystallized from the usual organic solvents because of its extreme insolubility, and high melting point, but the purity determined by TLC and later by CHN gave satisfactory result. We now describe a new, efficient, clean and simple method for preparing oestralactone which can obtained in high yield and pure form. The purification of oestralactone at the beginning was difficult due to its extreme insolubility, but by increasing the reaction time from five to seven days, the starting material (oestrone) totally disappeared. However, the estralactone does not need any further purification by chromatography, because it is clean and no by-products were formed in the reaction under these mild conditions.

The reaction involved the cleavage of ring D, either between carbon atoms 16 and 17 or, more probably, 13 and 17, followed by the addition of the elements of hydrogen peroxide to give an intermediate dihydroxy acid, which lactonized on acidification of the reaction mixture to form estralactone (equation 1).

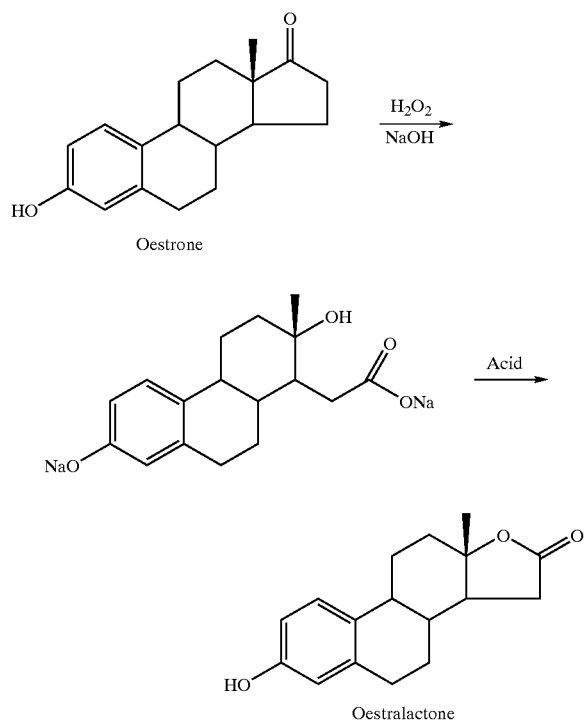

Westerfeld assumed the structure of the estralactone D-ring to be structure A not B on the basis that in lactone A, the parent hydroxyl group is tertiary and the carboxyl is at the end of a chain; in lactone B, the parent hydroxyl is primary and the carboxyl group is linked to a tertiary carbon which will not esterify with alcohol in the presence of catalyst such as HCl or $H_2SO_{4-}$. But lactone A could be methylated under these conditions and is, therefore, more compatible with the structure A. Later Wendler et alt.[6] and Murray et al.[7] supported his assumption as the structure of estralactone D-ring is structure A.

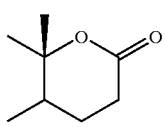

[A]

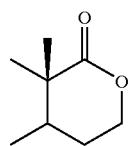

[B]

Our study is the first to provide modern spectroscopic date for estralactone and the NMR data were fully analysed by using $H^1$—$H^1$ Cosy and $H^1$—$C^{13}$ Cosy and are consistent with the structure A.

Heating is required to dissolve the oestralactone in DMF (the reaction solvent used for Sulphamylation) for preparation of estralactone sulphamate [2].

Oestralactone (1)[a]

Oestrone (3.0 g. 11.095 mnmol) was dissolved in 1N NaOH (600 ml) by heating. After cooling to room temperature, a solution of 6% $H_2O_2$ (127 ml) was added, and the reaction was allowed to proceed at room temperature for 7 days. The solution was acidified with HCl and the precipitate was collected by filtration, washed with water and dried to give a white solids (3.2 g) mp.=327–330° C., which was fractionated by flash chromatography with chloroform/acetone (8:1). The second fraction was collected and upon evaporation gives 1 as white solid (2.67 g, 84%). mp.= 335–340° C. (lit. 335–340° C.). vmax (KBr) 3220 (OH), 1680 (C=O) cm$^{-1}$. $\delta_H$ (DMSO-d$_6$, 400 MHz) 1.12–1.27 (6H, m, C-18-CH$_3$, C-8-H, C-15-H$_{ax}$ and C-7-H$_{ax}$), 1.53 ( 2H, m, C-9-H and C-12-H$_{ax}$), 1.74 (1H, m, C-16-H$_{ax}$), 1.95 (3H, m, C-16-H$_{eq}$, C-12-H$_{eq}$and C-7-H$_{eq}$) 2.36 (1H, m, C-14-H), 2.42 (1H, m, C-15-H$_{eq}$), 2.47 (1H, m, C-11-H$_{ax}$), 2.66 (1H, m, C-11-H$_{eq}$), 2.72 (2H, m, C-6-H$_2$), 6.45 (1H, d, $J_{C-4-H\ and\ C-2-H}$=2.44 Hz, C-4-H), 6.53 (1H, dd, $J_{C-2-H\ and\ C-1-H}$=8.24 Hz and $J_{C-2-H\ and\ C-4-H}$=2.14 Hz, C-2-H), 7.06 (1H, d, $J_{C-1-H\ and\ C-2-H}$=8.55 Hz) and 9.68 (1H, br s, C-3-OH), $^{13}$C (DMSO-d$_6$) 19.0 (C-12), 19.82 (C-18), 25.5 (C-7), 26.94 (C-15), 28.11 (C-11), 29.21 (C-6), 38.75 (C-16), 40.76 (C-8), 42.04 (C-14), 44.28 (C-9), 82.7 (C-13), 112.8 (C-2), 114.57 (C4), 126.06 (C-1), 129.41 (C-5 or C-10), 136.89 (C-10 or C-5), 155.01 (C-3), and 170.57 (C=O). MS: m/z (+ve ion FAB in m-NBA, rel. intensity) 287.1 [90, (M+H)$^+$], 274.1 (50), 255.2 (100), 243.2 (55), 226.0 (30), 211.1 (45), 195.0 (40), 183.0 (65), 173.1 (100), 164.0 (60), 147.1 (45), 133.0 (90), 111.1 (80), 97.1 (90), 80.1 (45) and 64.0 (65). Acc. MS: m/z (FAB)$^+$287.1596 $C_{18}H_{23}O_3$ requires 287.1647. Found C, 74.4; H 7.68 $C_{18}H_{23}O_3$ requires C, 75.5; H, 7.74%.

Oestralactone-3-O-sulphatemate (2)

Oestralactone (527 mg, 1.84 mmol), was added to anhydrous DMF (50 ml) and heated till it dissolved. The reaction mixture was cooled to room temperature, then sodium hydride (110 mg, 1.5 eq.) was added in small portions and the reaction mixture was stirred under N$_2$ for half an hour, when a concentrated sulphomyl chloride solution in toluene (5 eq.) was added. The reaction mixture was stirred overnight, poured into brine and extracted with ethyl acetate which was then washed with water, dried (MgSO$_4$) and after evaporation of the solvent, gave beige residue (616 mg), which was fractionated by flash chromatography with chloroform/acetone (8:1); the second fraction was collected and upon evaporation gave a white solid (436 mg), which was recrystallized from acetone/hexane (2:1) to give 2 as white crystals (360 mg, 54%) mp=217–219° C. IR vmax (KBr) 3320 and 3220 (NH), 1690 (C=O), 1390 (—SO$_2$—) cm$^{-1}$. $\delta_H$ (DMSO-d$_6$, 400 MHz) 1.13–1.36 (6H, m, C-18-CH$_3$, C-8-H, C-15-H$_{ax}$ and C-7-H$_{ax}$), 1.56 (2H, m, C-9-H and C-12-H$_{ax}$), 1.78 (1H, m, C-16-H$_{ax}$), 2.0 (3H, m, C-16-H$_{eq}$. C-12-H$_{eq}$ and C-7-H$_{eq}$), 2.47 (3H, m, C-14-H, C-15-H$_{eq}$ and C-11-H$_{ax}$), 2.69 (1H, m, C-11-H$_{eq}$), 2.84 (2H, m, C-6-H$_2$), 6.98 (1H, d $J_{C-4-H\ and\ C-2-H}$=2.44 Hz, C-4-H), 7.03 (1H, dd, $J_{C-2-H\ and\ C-1-H}$=8.79 Hz and $J_{C-2-H\ and\ C-4-H}$=2.44 Hz, C-2-H), 7.37 (1H, d, $J_{C-1-H\ and\ C-2-H}$=8.79 Hz, C-1-H) and 7.91 (2H, br s, exchanged with D$_2$O, C-3SO$_2$NH$_3$).

$^{13}$C (DMSO-d$_6$) 19.0 (C-12), 19.79 (C-18), 25.15 (C-7), 26.72 (C-15), 28.11 (C-11), 29.06 (C-6), 38.81 (C-16), 40.25 (C-8), 42.04 (C-14), 44.24 (C-9), 82.53 (C-13), 119.26 (C-2), 121.54 (C-4), 126.59 (C-1), 137.45 (C-5 or C-10), 137.78 (C-10 or C-5), 148.01 (C-3) and 170.53 (C=O). MS:

m/z (+ve ion FAR in m-NBA, rel. intensity) 366.1 [100, (M+H)⁺], 287.1 [25, (M+H–SO₂NH₂)⁺], 272.1 (20), 255.2 (45), 243.2 (55), 226.1 (15), 211.1 (25), 197.1 (20), 173.0 (65), 157.1 (30), 131.1 (45), 111.1(40), 97.1 (55), 80.1 (25) and 64.1 (30). MS: m/z (–ve ion FAB in m-NBA, rel. intensity) 518.3 [50, (M+NBA)]364.1 [100, (M–H)], 335.0 (20), 317.0 (15), 292.0 (15), 276.0 (30), 258.0 (15), 243.0 (5), 222.0 (10), 198.0 (10), 181.0 (15), 149.0 (5), 139.0 (15), 120.0 (10), 106.0 (15) and 78.0 (20). Acc. MS: m/z (FAB)⁺ 366.1389 $C_{18}H_{24}NO_5S$ requires 366.1376. Found C, 59.2; H, 6.39 $C_{18}H_{23}NO_5S$ requires C, 55.16; H, 6.34%.

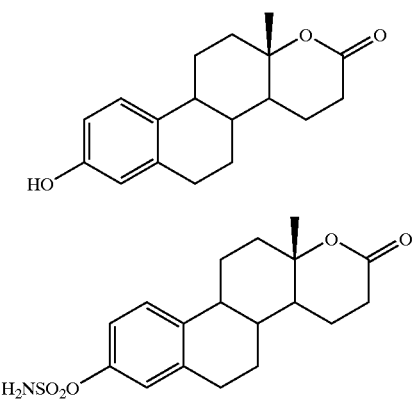

[1]ᵃ

[2]

REFERENCES

1) Gardner et al, *Biochem. J.*, 7, 588 (1914).
2) Westerfeld, *J. Biol. Chem.*, 143, 177 (1942).
3) Jacobsen et al, *J. Biol. Chem.*, 171, 61 (1947).
4) Peterson et al., *J. Am. Chem. Soc.*, 75, 5768 (1953).
5) Fried et al., *J. Am. Chem. Soc.*, 75, 5764 (1953).
6) Wendler et al., *J. Am. Chem. Soc.*, 77, 3559 (1955).
7) Murray et al., *J. Am. Chem. Soc.*, 78, 981–84 (1956).

EXAMPLE 4

ESTRALACTAM-3-O-SULPHAMATE

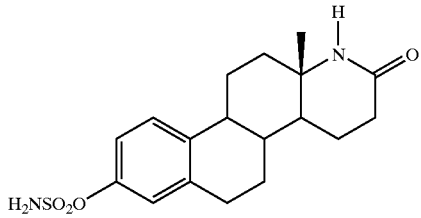

| INHIBITOR CONCENTRATION | % INHIBITION (mean ± S.D., n = 3) | |
|---|---|---|
| | MCF-7 cells | PLACENTAL MICROSOMES |
| 10 µM | 97.3 ± 1.2 | — |
| 1 µM | 94.0 ± 0.8 | — |
| 0.1 µM | 90.8 ± 3.1 | — |

In Vivo Inhibition (Rat Liver Sulphatase)
99.4±0.07% @ 2 mg/Kg/d×5 d, ORAL DOSE

EXAMPLE 5

ESTRALACTAM-3-O-SULPHAMATE

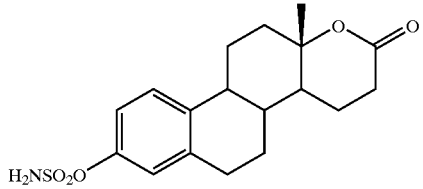

| INHIBITOR CONCENTRATION | % INHIBITION ($\bar{x}$ ± S.D., n = 3) | |
|---|---|---|
| | MCF-7 cells | PLACENTAL MICROSOMES |
| 10 µM | >99 | 96.6 ± 0.1 |
| 1 µM | 98.4 ± 0.8 | 84.1 ± 0.6 |
| 0.1 µM | 97.9 ± 1.3 | 34.0 ± 0.6 |
| 10 nM | 97.0 ± 0.6 | 13.9 ± 1.7 |
| 1 nM | 78.6 ± 2.3 | 7.4 ± 2.5 |
| 0.1 nM | 23.5 ± 3.7 | — |
| 10 pM | 3.7 ± 0.5 | — |

In Vivo Inhibition (Rat Liver Sulphatase)
98.2±1.7% @ 2 mg/Kg/day×5 days, ORAL DOSE
(cf. 99.1±0.2% for EMATE @ same dosage regimen)
Examples 2 to 5 are further referenced in Annex 1.

EXAMPLE 6

In Vivo Oestrogenicity

Compounds according to the present invention such as Compounds 2 and 4 (such as at 0.1 mg/Kg/day for five days) are administered orally to rats with another group of aninals receiving vehicle only (propylene glycol). At the end of the study uteri are obtained and weighed with the results being expressed as uterine weight/whole body weight×100.

Administration of Compounds 2 and 4 had no effect on uterine growth, showing that the Compounds are not oestrogenic.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

ANNEX 1

EXAMPLE 2

Oestralactam

Initially, we prepared oestrone oxime according to the method described[3], but we used hydroxylamine hydrochloride instead of hydroxylamiine acetate and obtained oestrone oxime in excellent yield, better than previously reported.

Of two possible geometrical isomers for 17-oximes, Wataru et al.[4] assumed they had the anti-form, because it is believed that this form of oximes[5] is more stable than the syn-form and that the transition state leading to the anti-oxime may have an energy lower than that in the case of the syn-isomer. Thus, the structure of the oestrone oxime isomer obtained was just assumed, and not confurmed by any special method such as NOE or X-ray crystallography. To prove and confirm which isomer was obtained from the reaction, we ran NOE experiment which did not work; perhaps because the hydroxyl group of the oxime is exchangeable. We proved the structure of oestrone oxime by X-ray crystallography and it was found indeed that only one geometrical isomer (anti-oxime isomer) was obtained.

Our study is the first to provide modern spectroscopic data and an X-ray crystal structure for oestrone oxime.

CHN analysis for oestrone oxime was alright, but by considering a small methanol content (from the crystallization solvent), which involved in hydrogen bonding to the molecule as X-ray shows, then the CHN values are very close.

The lactam form the anti-oxime of oestrone was prepared according to the method described[3] to give oestralactam2 as the only possible structure. Bernard et al.[3] proved the same structure by opening the lactam ring to form a primary carboxylic acid, not a tertiary carboxylic acid, as if the other isomer were formed. The primary carboxylic acid was readily esterified with methanol and an acid catalyst. But this was not enough evidence to prove the structure of oestrone lactam. Our modern methods to prove the structure of the oestrone oxime are more solid and show only the oestralactam.

Our study is also the first to provide modern spectroscopic data for oestralactam.

Due to the extremely insolubility of the oestrolactam and its high melting point, it could not be recrystallized from the usual organic solvents, and purity determination by TLC and accurate mass spectroscopy was correct, but CHN values is quite out of the range, although if we consider the presence of two molecules of methanol from the solvent by hydrogen bonding to the phenol of ring A and to the proton of the lactam of ring D, which is certainly feasible, as happens in oestrone oxime by X-ray crystal structure, the CHN is alright. Heating is required to dissolve the oestrolactam in DMF (the reaction solvent of sulphamylation) to prepare oestralactam sulphamate [4].

Oestrone Oxime (1)

To a solution of oestrone (10 g, 36.982 mmol) in ethanol (300 ml), hydroxylamine hydrochloride (7.71 g, 111 mmol, 3 eq.), sodium hydroxide (3.0 g, 75 mmol, 2 eq.) and water (10 ml) were added. The mixture was refluxed for two hours. The cold mixture was poured into 1N HCl. The precipitate was filtered, washed with cold water and dried to give a white solid (10.132 g, 96%). For analysis, a sample was recrystallized from aqueous methanol to give 1 as colorless crystals. Mp.=249–251° C. (lit. Mp.=248–250° C. IR (KBr) 1690 (—C=N—) cm$^{-1}$. $\delta_H$ (DMSO-d$_6$, 400 MHz) 0.85 (3H, s, C-18-CH$_3$), 1.26–3.18 (15H, m), 6.44 (1H, d, $J_{C-4-H\ and\ C-2-H}$=2.13 Hz, C-4-H), 6.5 (1H, dd, $J_{C-2-H\ and\ C-1-H}$=8.24 Hz, and $J_{C-2-H\ and\ C-4-H}$=2.44 Hz, C-2-H), 7.04 (1H, d, $J_{C-1-H\ and\ C-2-H}$=8.55 Hz, C-1-H), 9.03 (1H, br s, C-3-OH) and 10.1 (1H, br s, C=N—OH). C$^{13}$ 167.99 (—C=N—), 155.025 (C-3), 137.103 (C-5 or C-10), 130.19 (C10 or C-5), 126.0 (C-1), 114.99 (C-4), 112.79 (C-2), 52.52 (C-8 or C-9 or C-14), 48.66 (CH$_3$ from methanol), 43.62 (C-8 or C-9 or C-14), 43.61 (C-13), 37.91 (C-8 or C-9 or C-14), 34.33, 29.13, 26.90, 25.99, 24.94 and 22.57 (C-6, C-7, C-11, C-12, C-15 and C-16) and 17.35 (C-18). MS: m/z (+ve ion FAB in m-NBA, rel. intensity) 439.3 [15, (M+H+NBA)$^+$], 286.3 [100, M+H)$^+$], 268.3 [20, (M–H$_2$O)], 243.2 (10), 178.2 (10), 159.1 (10), 133.1 (15), 102.0 (10) and 74.9 (10). MS: m/z (–ve ion FAB in m-NBA, rel. intensity) 437.3 [65, (M–H+NBA)$^+$], 284.2 [100, (M–H)], 258.1 (25), 229.1 (20), 215.1 (25), 195.1 (45), 178.1 (30), 139.1 (35), 108.0 (30) and 65.0 (10). Acc. MS: m/z (FAB)$^+$=286.18046 C$_{18}$H$_{24}$NO$_2$ requires 286.18072. Found C, 73.5; H, 8.27; N, 4.48; C$_{18}$H$_{23}$NO$_2$ requires C, 75.76; H, 8.12; N, 4.91.

3-Hydroxy-13α-amino-13,17-seco-1,3,5(10)-estratrien-17-oic 13,17-lactam (17a-Aza-D-homoestrone) (Oestronelactam) (3)

A solution of oestrone oxime (1.0 g, 3.504 mmol), in anhydrous dioxane (35 ml) at 40° C. was stirred as thionyl chloride (1 ml) was added dropwise. A white precipitate which became yellow and then light brown, formed as the temperature rose to 49° C. After stirring ten minutes longer, the reaction mixture was quenched and made slightly alkaline by slow addition of aqueous sodium hydrogencarbonate solution. The resulting precipitate was filtered, washed with water and dried to give a yellow solid. Then it was triturated with methanol for decolourizauion and discarded impurities used. The precipitate was filtered and dried to give the lactam 3 as an almost white powder (733 mg, 73%). mp.=>350° C. (lit. 373–377° C. (dec.)). IR (KBr) 1640 (—CO—) cm$^{-1}$. $\delta_H$ (DMSO-$_6$, 400 MHz) 1.07 (3H, s, C-18-CH$_3$), 1.12–2.71 (15H, m), 6.44 (1H, d, $J_{C-4-H\ and\ C-2-H}$=2.45 Hz, C-4-H), 6.51 (1H, dd, $J_{C-1-H\ and\ C-1-H}$=8.31 Hz and $J_{C-2-H\ and\ C-4-H}$=2.45 Hz, C-2-H), 7.05 (1H, d $J_{C-1-H\ and\ C-2-H}$=8.31 Hz, C-1H), 7.56 (1H, br s, NH) and 9.02 (1H, br s, C-3-OH). MS: m/z (+ve ion FAB in m-NBA, rel. intensity) 286.2 [100, (M+H)$^+$], 270.2 (10), 255.2 (15), 243.2 (10), 225.2 (5), 213.1 (5), 195.1 (5), 183.1 (10), 173.2 (15), 157.1 (10), 145.1 (10), 131.1 (10), 111.0 (10), 97.0 (15), 79.9 (10) and 63.9 (10). Acc. MS: m/z (FAB)$^+$= 286.1812 C$_{18}$H$_{24}$NO$_2$ requires 286.1807. Found C, 69.9; H, 7.44; N, 4.41; C$_{18}$H$_{23}$NO$_2$ requires C, 75.76; H, 8.12; N, 4.91.

3-O-Sulphamyl-13α-amino-13,17-seco-1,3,5(10)-estratrien-17-oic 13,17-lactamtt (4)

Oestronelactam (272 mg, 0.9544 mmol) was added to anhydrous DMF (50 ml) and was heated till dissolved, the reaction mixture cooled to room temperature, then sodium hydride (57 mg, 1.5 eq.) was added in small portions and the reaction mixture was stirred under N$_2$ for half an hour. A concentrated sulphomyl chloride solution in toluene (5 eq.) was added. The reaction mixture was stirred overnight, poured into brine and extracted with ethyl acetate which was then washed with water, dried (MgSO$_4$) and after evaporated the solvent, gave a crude product (330 mg) which was fractionated on silica (100 g) with chloroform/acetone gradient, and upon evaporation the second fraction oave beige residue (286 mg) which was recrystallized from acetone/hexane (1:2) to give 4 as almost white crystals (223 mg, 64%) mp.=>265° C. (dec.). IR (KBr) 3500 (NH$_2$) 1710(CO), 1470 (—SO$_2$—) cm$^{-1}$. $\delta_H$(DMSO-d$_6$, 400 MHz) 1.1 (3H, s, C-18-CH$_3$), 1.21–2.9 (15H, m), 6.98 (1H, d, $J_{C-4-H\ and\ C-2-H}$=2.14 Hz, C-4-H), 7.02 (1H, dd, $J_{C-2-H\ and\ C-1-H}$=8.54 Hz and $J_{C-2-H\ and\ C-4-H}$=2.14 Hz, C-2-H), 7.35 (1H, d, $J_{C-1-H\ and\ C-2-H}$=8.54 Hz, C-1-H), 7.6 (1H, br s, NH) and 7.94 (2H, s, exchanged with D$_2$O, C-3-SO$_2$NH$_2$). MS: m/z (+ve ion FAB in m-NBA, rel. intensity) 365.2 [100, (M+H)$^+$], 349.2 (20), 330.1 (25), 319.1 (10), 306.1 (15), 287.1 [10, (M+H–SO$_2$NH$_2$)$^+$]. MS: m/z (–ve ion FAB in m-NBA, rel. intensity) 517.2 [50, (M+NBA)$^+$], 363.1 [100, (M–H)], 341.0 (30), 292.1 (20), 276.1 (40), 258.0 (35). Acc. MS: m/z (FAB)$^+$=365.1550 C$_{18}$H$_{25}$N$_2$O$_4$S requires 365.1535. Found C, 58.9; H, 6.61; N, 7.36; C$_{18}$H$_{23}$N$_2$O$_2$S requires C, 59.32; H, 6.64; N, 7.69.

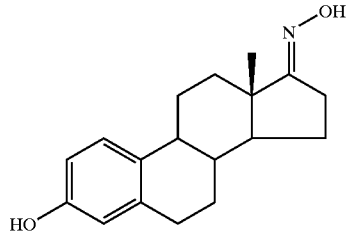

[1]

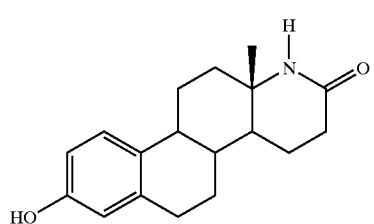

[3]

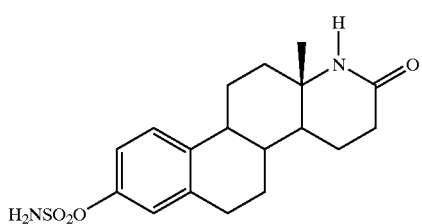

[4]

REFERENCES

1) Ivanenko T I, Kolomin L V Golubovskaya L E and Pivnitskii K K Synthesis and properties of 17-N-Substituted derivatives of 1,3,5 (10)-estratrienes. *Pharm. Chem. J.* 1982, 16, 751–56.
2) Peters R H, Crowe D F, Mitchell A A, Chong W K M and Tanabe M. 17-Desoxy estrogen analogues. *J Med. Chem.* 1989, 32, 1642–52.
3) Bernard M R and Hayes F N 17- and 17a-D-homosteroids. *Journal of American Chemical Society* 1955, 78, 639–643.
4) Nagata W, Sugasawa T, Narisada M, Okada T, Sasakura K, Murakami M and Hayase Y. Steroids and their O-alkyl derivatives. *Chem. Pharm. Bull.* 1966, 14, 174–186.
5) Kaufmnann C S Beckman rearrangement of 17-keto steroids oximes. *J Am. Chem. Soc.* 1951, 73, 1779.

EXAMPLE 3
Steroid Lactones

The oxidation of a steroid ring ketone to a lactone was first reported by Garder and Godden using ammoniun persulphate for oxidation of coprostan-3-one.

The conversion of a 17-keto steroid to a D ring lactone was first reported by Westerfeld[2] who oxidised estrone with alkaline hvdrogen peroxide. Subsequently, Jacobsen[3] oxidised oestrone with peracid in acetic acid to a lactone which was chemically similar to westerfeld's lactone [1][a] but different in its physiological properties. Several related lactones have been also prepared by the microbiological oxidation of steroids[4,5].

Our modification of Westerfeld method[2] by using milder conditions and a longer reaction time oave estralactone in excellent yield (84%), the best and highest yield reported so far. Briefly, treatment of oestrone with alkaline 6% hydrogen peroxide instead of 10% for 5–7 days not for 3 days at room temperature gave estralactone in high yield. The estralactone could not recrystallized from the usual organic solvents because of its extreme insolubility, and high melting point, but the purity determined by TLC and later by CHN gave satisfactory result. We now describe a new, efficient, clean and simple method for preparing oestralactone which can obtained in high yield and pure form. The purification of oestralactone at the beginning was difficult due to its extreme insolubility, but by increasing the reaction time from five to seven days, the starting material (oestrone) totally disappeared. However, the estralactone does not need any further purification by chromatography, because it is clean and no by-products were formed in the reaction under these mild conditions.

The reaction involved the cleavage of ring D, either between carbon atoms 16 and 17 or, more probably, 13 and 17, followed by the addition of the elements of hydrogen peroxide to give an intermediate dihydroxy acid, which lactonized on acidification of the reaction mixture to form estralactone (equation 1).

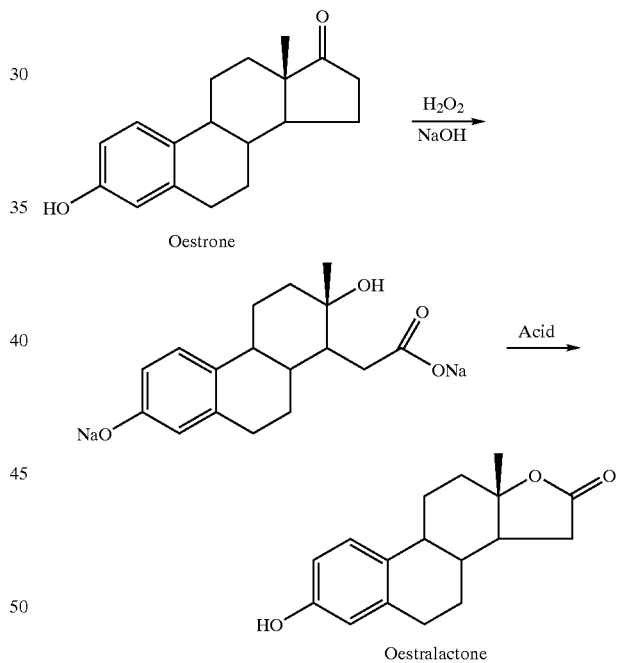

Westerfeld assumed the structure of the estralactone D-ring to be structure A not B on the basis that in lactone A, the parent hydroxyl group is tertiary and the carboxyl is at the end of a chain; in lactone B, the parent hydroxyl is primary and the carboxyl group is linked to a tertiary carbon which will not esterify with alcohol in the presence of catalyst such as HCl or $H_2SO_{4-}$. But lactone A could be methylated under these conditions and is, therefore, more compatible with the structure A. Later Wendler et al.[6] and Murray et al.[7] supported his assumption as the structure of estralactone D-ring is structure A.

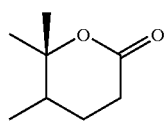

[A]

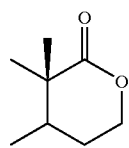

[B]

Our study is the first to provide modern spectroscopic date for estralactone and the NMR data were fully analysed by using $H^1$—$H^1$ Cosy and $H^1$—$C^{13}$ Cosy and are consistent with the structure A.

Heating is required to dissolve the oestralactone in DMF (the reaction solvent used for Sulphamylation) for preparation of estralactone sulphamate [2].

Oestralactone (1)[a]

Oestrone (3.0 g. 11.095 mmol) was dissolved in 1N NaOH (600 ml) by heating. After cooling to room temperature, a solution of 6% $H_2O_2$ (127 ml) was added, and the reaction was allowed to proceed at room temperature for 7 days. The solution was acidified with HCl and the precipitate was collected by filtration, washed with water and dried to give a white solids (3.2 g) mp.=327–330° C., which was fractionated by flash chromatography with chloroform/acetone (8:1). The second fraction was collected and upon evaporation gives 1 as white solid (2.67 g, 84%). mp=335–340° C. (lit. 335–340° C.). vmax (KBr) 3220 (OH), 1680 (C=O) cm$^{-1}$. $\delta_H$ (DMSO-d$_6$, 400 MHz) 1.12–1.27 (6H, m, C-18-CH$_3$, C-8-H, C-15-H$_{ax}$ and C-7-H$_{ax}$), 1.53 (2H, m, C-9-H and C-12-H$_{ax}$), 1.74 (1H, m, C-16-H$_{ax}$), 1.95 (3H, m, C-16-H$_{eq}$, C-12-H$_{eq}$, and C-7-H$_{eq}$), 2.36 (1H, m, C-14-H), 2.42 (1H, m, C-15-H$_{eq}$), 2.47 (1H, m, C-11-H$_{ax}$), 2.66 (1H, m, C-11-H$_{eq}$), 2.72 (2H, m, C-6-H$_2$), 6.45 (1H, d, $J_{C\text{-}4\text{-}H\ and\ C\text{-}2\text{-}H}$=2.44 Hz, C-4-H), 6.53 )1H, dd, $J_{C\text{-}2\text{-}H\ and\ C\text{-}1\text{-}H}$=8.24 Hz and $J_{C\text{-}2\text{-}H\ and\ C\text{-}4\text{-}H}$=2.14 Hz, C-2-H), 7.06 (1H, d, $J_{C\text{-}1\text{-}H\ and\ C\text{-}2\text{-}H}$=8.55 Hz) and 9.68 (1H, br s, C-3-OH), $^{13}$C (DMSO-d$_6$) 19.0 (C-12), 19.82 (C-18), 25.5 (C-7), 26.94 (C-15), 28.11 (C-11), 29.21 (C-6), 38.75 (C-16), 40.76 (C-8), 42.04 (C-14), 44.28 (C-9), 82.7 (C-13), 112.8 (C-2), 114.57 (C4), 126.06 (C-1), 129.41 (C-5 or C-10), 136.89 (C-10 or C-5), 155.01 (C-3), and 170.57 (C=O). MS: m/z (+ve ion FAB in m-NBA, rel. intensity) 287.1 [90, (M+H)$^+$], 274.1 (50), 255.2 (100), 243.2 (55), 226.0 (30), 211.1 (45), 195.0 (40), 183.0 (65), 173.1 (100), 164.0 (60), 147.1 (45), 133.0 (90), 111.1 (80), 97.1 (90), 80.1 (45) and 64.0 (65). Acc. MS: m/z (FAB)$^+$287.1596 C$_{18}$H$_{23}$O$_3$ requires 287.1647. Found C, 74.4; H, 7.68 C$_{18}$H$_{22}$O$_3$ requires C, 75.5; H, 7.74%.

Oestralactone-3-O-sulphatemate (2)

Oestralactone (527 mg, 1.84 mmol), was added to anhydrous DMF (50 ml) and heated till it dissolved. The reaction mixture was cooled to room temperature, then sodium hydride (110 mg, 1.5 eq.) was added in small portions and the reaction mixture was stirred under $N_2$ for half an hour, when a concentrated sulphomyl chloride solution in toluene (5 eq.) was added. The reaction nixture was stirred overnight, poured into brine and extracted with ethyl acetate which was then washed with water, dried (MgSO$_4$) and after evaporation of the solvent, gave beige residue (616 mg), which was fractionated by flash chromatography with chloroform/acetone (8:1); the second fraction was collected and upon evaporation gave a white solid (436 mg), which was recrystallized from acetone/hexane (2:1) to give 2 as white crystals (360 mg, 54%) mp=217–219° C. IR vmax (KBr) 3320 and 3220 (NH), 1690 (C=O), 1390 (—SO$_2$—) cm$^{-1}$. $\delta_H$ (DMSO-$_6$, 400 MHz) 1.13–1.36(6H, m, C-18-H$_3$, C-8-H, C-15-H$_{ax}$ and C-7-H$_{ax}$), 1.56 (2H, m, C-9-H and C-12-H$_{ax}$), 1.78 (1H, m, C-16-H$_{ax}$), 2.0 (3H, m, C-16-H$_{eq}$, C-12-H$_{eq}$ and C-7-H$_{eq}$), 2.47 (3H, m, C-14-H. C-15-H$_{eq}$ and C-11-H$_{ax}$), 2.69 (1H, m, C-11-H$_{eq}$), 2.84 (2H, m, C-6-H$_2$), 6.98 (1H, d, $J_{C\text{-}4\text{-}H\ and\ C\text{-}2\text{-}H}$=2.44 Hz, C-4-H), 7.03 (1H, dd, $J_{C\text{-}2\text{-}H\ and\ C\text{-}1\text{-}H}$=8.79 Hz, and $J_{C\text{-}2\text{-}H\ and\ C\text{-}4\text{-}H}$=2.44 Hz, C-2-H), 7.37 (1H, d, $J_{C\text{-}1\text{-}H\ and\ C\text{-}2\text{-}H}$=8.79 Hz, C-1-H) and 7.91 (2H, br s, exchanged with D$_2$O, C-3SO$_2$NH$_2$).

$^{13}$C (DMSO-d$_6$) 19.0 (C-12), 19.79 (C-18), 25.15 (C-7), 26.72 (C-15), 28.11 (C-11), 29.06 (C-6), 38.81 (C-16), 40.25 (C-8), 42.04 (C-14), 44.24 (C-9), 82.53 (C-13), 119.26 (C-2), 121.54 (C-4), 126.59 (C-1), 137.45 (C-5 or C-10), 137.78 (C-10 or C-5), 148.01 (C-3) and 170.53 (C=O). MS: m/z (+ve ion FAB in m-NBA, rel. intensity) 366.1 [100, (M+H)$^+$], 287.1 [25, (M+H–SO$_2$NH$_2$)$^+$], 272.1 (20), 255.2 (45), 243.2 (55), 226.1 (15), 211.1 (25), 197.1 (20), 173.0 (65), 157.1 (30), 131.1 (45), 111.1 (40), 97.1 (55), 80.1 (25) and 64.1 (30). MS: m/z (–ve ion FAB in m-NBA, rel. intensity) 518.3 [50, (M+NBA)]364.1 [100, (M–H)], 335.0 (20), 317.0 (15), 292.0 (15), 276.0 (30), 258.0 (15), 243.0 (5), 222.0 (10), 198.0 (10), 181.0 (15), 149.0 (5), 139.0 (15), 120.0 (10), 106.0 (15) and 78.0 (20). Acc. MS: m/z (FAB)$^+$ 366.1389 C$_{18}$H$_{24}$NO$_5$S requires 366.1376. Found C, 59.2; H, 6.39 C$_{18}$H$_{23}$NO$_5$S requires C, 55.16; H, 6.34%.

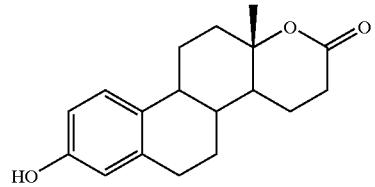

[1][a]

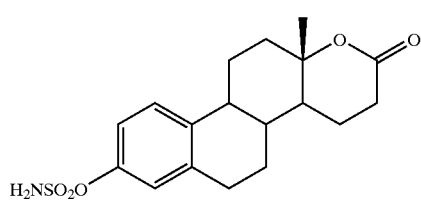

[2]

REFERENCES

1) Gardner et al, *Biochem. J.*, 7, 588 (1914).
2) Westerfeld, *J. Biol. Chem.*, 143, 177 (1942).
3) Jacobsen et al, *J. Biol. Chem.*, 171, 61 (1947).
4) Peterson et al., *J. Am. Chem. Soc.*, 75, 5768 (1953).
5) Fried et al., *J. Am. Chem. Soc.*, 75, 5764 (1953).
6) Wendler et al., *J. Am. Chem. Soc.*, 77, 3559 (1955).
7) Murray et al., *J. Am. Chem. Soc.*, 78, 981–84 (1956).

EXAMPLE 4

ESTRALACTANE-3-O-SULPHAMATE

|  | % INHIBITION (mean ± S.D., n = 3) | |
|---|---|---|
| INHIBITOR CONCENTRATION | MCF-7 cells | PLACENTAL MICROSOMES |
| 10 $\mu$M | 97.3 ± 1.2 | — |
| 1 $\mu$M | 94.0 ± 0.8 | — |
| 0.1 $\mu$M | 90.8 ± 3.1 | — |

In Vivo Inhibition (Rat Liver Sulphatase)
99.4±0.07% @ 2 mg/Kg/d×5 d, ORAL DOSE

EXAMPLE 5

ESTRALACTAM-3-O-SULPHAMATE

|  | % INHIBITION ($\bar{x}$ ± S.D., n = 3) | |
|---|---|---|
| INHIBITOR CONCENTRATION | MCF-7 cells | PLACENTAL MICROSOMES |
| 10 $\mu$M | >99 | 96.6 ± 0.1 |
| 1 $\mu$M | 98.4 ± 0.8 | 84.1 ± 0.6 |
| 0.1 $\mu$M | 97.9 ± 1.3 | 34.0 ± 0.6 |
| 10 nM | 97.0 ± 0.6 | 13.9 ± 1.7 |
| 1 nM | 78.6 ± 2.3 | 7.4 ± 2.5 |
| 0.1 nM | 23.5 ± 3.7 | — |
| 10 pM | 3.7 ± 0.5 | — |

In Vivo Inhibition (Rat Liver Sulphatase)
98.2±1.7% @ 2mg/Kg/day×5 days, ORAL DOSE
(cf. 99.1±0.2% for EMATE @ same dosage regimen)

What is claimed is:

1. A sulphamate compound having a formula:

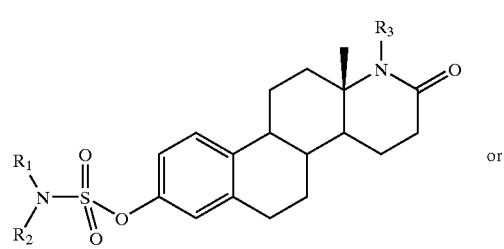

(A)

or

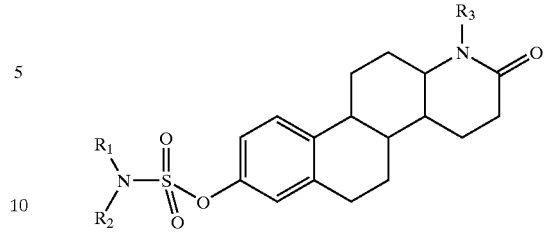

(B)

wherein $R_1$ and $R_2$ are independently H or alkyl and $R_3$ is alkyl.

2. The sulphamate compound (A) of claim 1 wherein $R_1$ is H, $R_2$ is H, and $R_3$ is alkyl.

3. The sulphamate compound (B) of claim 1 wherein $R_1$ is H, $R_2$ is H, and $R_3$ is alkyl.

4. The sulphamate compound (A) of claim 1 wherein $R_1$ is H, $R_2$ is alkyl, and $R_3$ is alkyl.

5. The sulphamate compound (B) of claim 1 wherein $R_1$ is H, $R_2$ is alkyl, and $R_3$ is alkyl.

6. The sulphamate compound (A) of claim 1 wherein $R_1$ is alkyl, $R_2$ is alkyl, and $R_3$ is alkyl.

7. The sulphamate compound (B) of claim 1 wherein $R_1$ is alkyl, $R_2$ is alkyl, and $R_3$ is alkyl.

8. The sulphamate compound (A) of claim 1 wherein $R_1$ is alkyl, $R_2$ is H, and $R_3$ is alkyl.

9. The sulphamate compound (B) of claim 1 wherein $R_1$ is alkyl, $R_2$ is H, and $R_3$ is alkyl.

10. The sulphamate compound (A) of claim 1 wherein $R_1$ and $R_2$ are independently H or $C_1$–$C_{10}$ alkyl and $R_3$ is $C_1$–$C_{10}$ alkyl.

11. The sulphamate compound (B) of claim 1 wherein $R_1$ and $R_2$ are independently H or $C_1$–$C_{10}$ alkyl and $R_3$ is $C_1$–$C_{10}$ alkyl.

12. The sulphamate compound (A) of claim 1 wherein $R_1$ and $R_2$ are independently H or $C_1$–$C_5$ alkyl and $R_3$ is $C_1$–$C_5$ alkyl.

13. The sulphamate compound (B) of claim 1 wherein $R_1$ and $R_2$ are independently H or $C_1$–$C_5$ alkyl and $R_3$ is $C_1$–$C_5$ alkyl.

14. The sulphamate compound (A) of claim 1 wherein $R_1$ is H, $R_2$ is H, and $R_3$ is $C_1$–$C_{10}$ alkyl.

15. The sulphamate compound (A) of claim 1 wherein $R_1$ is H, $R_2$ is $C_1$–$C_{10}$ alkyl, and $R_3$ is $C_1$–$C_{10}$ alkyl.

16. The sulphamate compound (A) of claim 1 wherein $R_1$ is $C_1$–$C_{10}$ alkyl, $R_2$ is $C_1$–$C_{10}$ alkyl, and $R_3$ is $C_1$–$C_{10}$ alkyl.

17. The sulphamate compound (A) of claim 1 wherein $R_1$ is $C_1$–$C_{10}$ alkyl, $R_2$ is H, and $R_3$ is $C_1$–$C_{10}$ alkyl.

18. A method of inhibiting oestrone sulphatase comprising administering to a subject in need thereof an oestrone sulphatase inhibiting amount of the compound of any one of claims 1, 2–7, 8–16, and 17, or a pharmaceutically or veterinarily acceptable salt thereof.

19. A pharmaceutical or veterinary composition comprising the compound of any one of claim 1, 2–7, 8–16 and 17, or a pharmaceutically or veterinarily acceptable salt thereof, and a pharmaceutically or veterinarily acceptable diluent, carrier, or excipient.

* * * * *

UNITED STATES PATENT AND TRADEMARK OFFICE
CERTIFICATE OF CORRECTION

| | |
|---|---|
| PATENT NO. | : 6,949,561 B1 |
| DATED | : September 27, 2005 |
| INVENTOR(S) | : Michael John Reed et al. |

It is certified that error appears in the above-identified patent and that said Letters Patent is hereby corrected as shown below:

<u>Column 26,</u>
Line 62, "claim" should read -- claims 1, 2-7, 8-16 and 17, --.

Signed and Sealed this

Twentieth Day of December, 2005

JON W. DUDAS
*Director of the United States Patent and Trademark Office*